United States Patent [19]
Fink et al.

[11] Patent Number: 5,686,262
[45] Date of Patent: *Nov. 11, 1997

[54] RECYCLE PROCESS FOR THE PRODUCTION OF LOW-COST SOLUBLE COLLAGEN

[75] Inventors: David J. Fink, Shaker Heights; Richard S. Brody, Worthington, both of Ohio

[73] Assignee: Ranpak Corporation, Concord, Ohio

[*] Notice: The term of this patent shall not extend beyond the expiration date of Pat. No. 5,460,967.

[21] Appl. No.: 488,368

[22] Filed: Jun. 7, 1995

Related U.S. Application Data

[60] Division of Ser. No. 250,803, May 27, 1994, Pat. No. 5,460,967, which is a continuation-in-part of Ser. No. 78,932, Jun. 16, 1993, Pat. No. 5,316,942.

[51] Int. Cl.$^6$ .............................. D21H 17/00; C07K 3/12; C12P 21/00; C12P 21/06
[52] U.S. Cl. .............. 435/68.1; 106/124; 106/125; 106/127; 106/135; 162/135; 162/143; 162/151; 162/157.6; 162/174; 162/180; 162/183; 162/184; 162/185; 435/71.1; 435/184; 435/212; 435/213; 435/273; 536/356
[58] Field of Search ................... 435/68.1, 213, 435/219, 273, 71.1, 212; 162/174, 135, 143, 151, 157.6, 180, 183, 184, 185; 536/356; 106/124, 125, 127, 135

[56] References Cited

U.S. PATENT DOCUMENTS

| | | | |
|---|---|---|---|
| 1,184,518 | 5/1916 | Clapp . | |
| 2,352,922 | 7/1944 | Thomas et al. | 92/21 |
| 2,637,321 | 9/1953 | Cresswell | 128/335.5 |
| 2,934,446 | 4/1960 | Highberger et al. | 106/155 |
| 2,934,447 | 4/1960 | Highberger et al. | 106/155 |
| 3,223,551 | 12/1965 | Tu | 117/140 |
| 3,314,861 | 4/1967 | Fujii | 195/6 |
| 3,532,593 | 10/1970 | Young | 162/2 |
| 3,592,925 | 7/1971 | Evans et al. | 424/119 |
| 3,616,205 | 10/1971 | Ito et al. | 195/6 |
| 3,907,779 | 9/1975 | DeBoer et al. | 260/211.5 R |
| 4,066,083 | 1/1978 | Ries | 128/325 |
| 4,140,537 | 2/1979 | Luck et al. | 106/155 |
| 4,220,724 | 9/1980 | Berg et al. | 435/273 |
| 4,233,360 | 11/1980 | Luck et al. | 428/310 |
| 4,293,647 | 10/1981 | Monsheimu et al. | 435/69 |
| 4,389,487 | 6/1983 | Ries | 435/273 |
| 4,488,911 | 12/1984 | Luck et al. | 106/161 |
| 4,565,580 | 1/1986 | Miyata et al. | 106/124 |
| 4,575,500 | 3/1986 | Burg et al. | 214/121 |
| 4,655,980 | 4/1987 | Chu | 264/102 |
| 4,703,108 | 10/1987 | Silver et al. | 530/356 |
| 4,883,864 | 11/1989 | Scholz | 530/356 |
| 5,021,406 | 6/1991 | Maeda et al. | 54/99 |
| 5,137,875 | 8/1992 | Tsunenaga et al. | 514/21 |
| 5,316,942 | 5/1994 | Fink | 435/273 |

FOREIGN PATENT DOCUMENTS

| | | |
|---|---|---|
| 139458A | 5/1985 | European Pat. Off. . |
| 1145904 | 3/1963 | Germany . |
| 1062083 | 3/1967 | United Kingdom . |
| 2023613 | 1/1980 | United Kingdom . |
| 8103261 | 11/1981 | WIPO . |

OTHER PUBLICATIONS

Abstract 118126g, "Collagen & Collagen Solutions," Japan Leathaer Co., Ger. 1,145,904, Mar. 1963.
Hamill et al, "Glue as Beater Sizing," Paper Trade Journal, 55th year, pp. 32–37.
Calkin, "Modern Pulp & Papermaking," Reinhold Publishing Corp., pp. 269 and 312–313.
"Hide Glue for Tub Sizing," TAPPI, pp. 227–228.
"Relationship Between Collagen & Gelatin," pp. 152–153, 164–167, 176–177, 422–425.
The Preparation and Properties of Solubilised Collagens; N. T. Crosby et al; J. Soc. Lea. Trades Chemists; 46; 1962; pp. 152–161.
Comminuted Collagen: Estimated Costs of Commercial Production; V.A. Turkot et al; Food Technology; Apr. 1978; pp. 48–57.
The Use of Collagen Dispersions During the Manufacturing of Paper; J. Tkac et al; Kozarstvi 30; 11; 1980; pp. 324–326.
The Science & Technology of Gelatin; Ward, A.G. & Courts, A.; Academic Press; 1977; pp. 152–153, 164–167, 422–425.
New items of information submitted herewith.

Primary Examiner—Herbert J. Lilling
Attorney, Agent, or Firm—Renner, Otto, Boisselle & Sklar

[57] ABSTRACT

The invention includes a method that provides a low cost aqueous solution of solubilized collagen by the steps of: (a) providing an aqueous ground slurry of insoluble collagen and adjusting the pH of said slurry to obtain activity for a proteolytic enzyme added in Step b; (b) adding said proteolytic enzyme to said pH adjusted slurry; (c) reacting the slurry and enzyme of Step b and/or recycled insoluble collagen and enzyme from Step e at a temperature, T, and for a time, t, effective for forming a solution increased in solubilized collagen; (d) adding additional water and insoluble collagen to said solution of Step c and mixing; (e) separating at least some of the solution of Step d containing solubilized collagen from insoluble collagen, whereby at least a portion of said insoluble collagen and proteolytic enzyme is recycled to Step c, and the separated solution containing solubilized collagen is withdrawn as product; an alternative embodiment provides for the direct production of solubilized collagen without the recycle step.

52 Claims, 4 Drawing Sheets

RECYCLE PROCESS FOR THE PRODUCTION OF LOW-COST SOLUBLE COLLAGEN

This is a divisional of application Ser. No. 08/250,803 filed on May 27, 1994, now U.S. Pat. No. 5,460,967, which is a continuation-in-part application of Ser. No. 08/078,932 filed Jun. 16, 1993.

FIELD OF THE INVENTION

This invention relates to the low-cost production of solubilized collagen capable of improving binding between cellulosic particles. Solubilized collagen has utility in the production of paper from recycled fibers with higher strength, or as a binder for cellulosic materials.

The invention is related to the application entitled PAPER STRENGTHENED WITH SOLUBILIZED COLLAGEN AND METHOD having attorney docket number 21568(2)/2913, filed concurrently and having the same filing date as the present application, the disclosure of which is incorporated by reference herein.

BACKGROUND OF THE INVENTION

The processing of animal hides to produce leather is an ancient art, and today it is a very mature industry. Excellent references to the chemistry of leather manufacture by McLauglin, G. D., et al, *The Chemistry of Leather Manufacture*, Reinhold Publishing Corp, N.Y. (1945), and collagen reactivity by Gustavson, K. H., *The Chemistry and Reactivity of Collagen*, Academic Press Inc., N.Y. (1956), date from the 1940's and 1950's, and are still basic descriptions of the art practiced today. The name "collagen" is derived from the Greek word for glue, as is the term "colloid" which means "gluelike" in Greek.

Skin is composed of four distinct layers, which are, proceeding from outside-in: (1) a thin outer layer of epithelium termed the "epidermis", which is rich in the protein keratin, not collagen; (2) a dense collagen-rich layer, termed the "dermal" or "grain" layer, also called in the older literature the "thermostat' layer; (3) a thicker layer of less-dense, collagen-rich connective tissues, termed the "corium" layer; and (4) an inner layer of "subcutaneous tissue", known to the tanner as "flesh", by which the skin is attached to the underlying tissue.

Although hides may merely be "cured" in salt and/or other biocidal solutions to stop microbial degradation, many hides that are intended for use in leather manufacture are "limed", that is, soaked in a saturated solution of hydrated lime (calcium hydroxide) and water. The liming process initiates the loosening of the epidermis and the subcutaneous layer, and is the first step in the dehairing process. After liming is complete, the hair, epidermis, and any residual flesh, fat and surface muscles are removed by mechanical scraping, and the dermal layer is mechanically cut, along with enough of the corium layer to give the final leather its required thickness, from the remaining inner corium layer.

In leather-making the primary interest is on the dense collagen-rich dermal layer, which is about 25% of the thickness of the corium layer. During the process of leather-making, the dermal tissue receives separate chemical and tanning treatments to stabilize the collagen structure.

The residual portion of the corium layer that is separated from the dermal layer is termed the "limed split" and is a by-product waste of the leather manufacturing process. It is these limed splits that become, for example, the collagen-rich feedstock for sausage casing production, and that have been used as the source of collagen for the examples herein.

During the liming process, the skin imbibes and binds water, and becomes highly swollen; in the process it acquires a very alkaline pH of about 12.5. The chemistry of the liming process is quite well understood. Prior to further leather processing, and in the collagen production process considered here, the skins must be "delimed" by soaking in acid or salt solutions.

Four patents (U.S. Pat. Nos. 4,140,537, 4,233,360, 4,488,911, 4,655,980) all assigned to Collagen Corporation, describe enzymatic methods, including pepsin hydrolysis, for solubilizing collagen to produce a "non-immunogenic" soluble collagen, which is then converted to other forms for use as medical implants. In these patents, the initial soluble product is relatively low (for collagen) number average molecular weight aggregates (about 300,000 daltons); the objective is to remove all of the "telopeptides" which are found at the end of these chains. Higher molecular weight aggregates would not have the telopeptides completely removed, and would be more "immunogenic" by their standards.

A 1970 U.S. patent (U.S. Pat. No. 3,532,593) describes a method for making collagen for use in papermaking. It describes a mechanical method for isolating preexisting gelled collagen fibers, not an enzymatic method for solubilizing the collagen as in the present invention. This patent describes a method for adjusting the pH of mechanically gelled collagen to promote flotation of fat and for skimming the floating fat from the collagen. The patent also refers to the partial "gelatinizing" of the collagen by heating to improve the bonding properties of the additive, although the primary objective is to produce a fibrous product.

A French journal article by G. Sauret et al, Le collagne ans la fabrication du papier, Revue A.T.P.I., Vol 33, No. 8, Octobre 1979, pp 374–365, discloses a mechanical method using a Turmix-Waring blender for preparing collagen for use with strengthening paper.

The present invention proposes to overcome the disadvantages of the previous methods by preparing a low cost collagen with an enzymatic method. The low cost collagen being in a soluble form making it amenable to the use with paper.

SUMMARY OF THE INVENTION

A typical embodiment of the invention is a method for producing an aqueous solution of solubilized collagen by the steps of (a) providing an aqueous ground slurry of insoluble collagen and adjusting the pH of the slurry to obtain activity for a later added proteolytic enzyme; (b) adding the proteolytic enzyme to the pH adjusted slurry; (c) reacting the slurry and enzyme of step b and\or recycled insoluble collagen and enzyme of step e at a temperature, T, and for a time, t, effective for forming a solution increased in solubilized collagen; (d) adding additional water and insoluble collagen to the solution of step (c) and mixing; (e) separating at least some of the solution of step d containing solubilized collagen from the insoluble collagen, whereby at least a portion of the insoluble collagen and proteolytic enzyme is recycled to step c, and a separated solution containing solubilized collagen is withdrawn as product. Typically step c may be repeated two, three, four or more times. Additional enzyme may be added to the recycled insoluble collagen from step e that substantially replaces enzyme removed with the withdrawal of product or when the rate of reaction on recycling decreases below a predetermined level. In one typical embodiment, the method is operated as a continuous process. The reaction may typically be stopped by adjusting the pH to that where the proteolytic enzyme is substantially inactive; and/or by reducing the temperature to that where the proteolytic enzyme is substantially inactive. In another typical embodiment in step a, the liquid or solids content of the wet ground slurry is preferably adjusted so that the solids are at a concentration of about 0.1 to about 1.0 wt %; in step c the temperature, T, is preferably about 5° C. to about 30° C., and more preferably about 15° C. to about 28° C. In another preferred embodiment the solids concentration is between about 0.3 to 0.35 wt % and the reaction of step c is at a temperature of about 10° to about 30° C., and for a time of 10 to 72 hours; more preferably the temperature is between 15° C. and 28° C. Typical proteolytic enzymes are selected from the group consisting of porcine mucosal pepsin, bromelain, chymopapain, chymotrypsin, collagenase, ficin, papain, peptidase, proteinase A, proteinase K, trypsin, microbial protease, and combinations of such enzymes. More preferably the proteolytic enzyme is pepsin or a microbial acid protease. When porcine mucosal pepsin is selected the pH is preferably about 1.5–3.0, and the temperature about 15° C. to about 28° C. Typically, at least 80 wt % of the insoluble collagen is converted to soluble collagen and with a number average molecular weight 300,000 daltons and above; while more preferably at least 90 wt % of the insoluble collagen is converted to soluble collagen and the number average molecular weight is above 1,000,000 daltons.

A further typical embodiment of the invention includes a method for producing an aqueous solution of solubilized collagen by the steps of (a) providing an aqueous ground slurry of insoluble collagen; (b) adjusting the water or solid content of the wet ground slurry whereby the insoluble collagen is at a concentration that promotes substantially maximum solubilized collagen concentration in a final product; (c) adjusting the pH of the slurry from step b to obtain activity for a proteolytic enzyme added in step d; (d) adding and mixing the proteolytic enzyme with the pH adjusted slurry; (e) reacting the slurry of step d and\or the recycled insoluble collagen of step g at a temperature, T, and for a time, t, effective for forming a solution comprising solubilized collagen derived from the insoluble collagen particles; (f) adding additional water and insoluble collagen to the solution containing solubilized collagen in step e and mixing; (g) separating at least some of the solution of step f containing solubilized collagen from the insoluble collagen and returning the insoluble collagen to step e, whereby at least a portion of the proteolytic enzyme is recycled, and a separated solution containing solubilized collagen is withdrawn as product. Typically step e may be repeated two, three, four or more times. Additional enzyme may be added to the recycled insoluble collagen from step e that substantially replaces enzyme removed with the withdrawal of product or when the rate of reaction on recycling decreases below a predetermined level. In one typical embodiment, the method is operated as a continuous process. The reaction may typically be stopped by adjusting the pH to that where the proteolytic enzyme is substantially inactive; and/or by reducing the temperature to that where the proteolytic enzyme is substantially inactive. In another typical embodiment in step b, the liquid or solids content of the wet ground slurry is preferably adjusted so that the solids are at a concentration of about 0.1 to about 1.0 wt %; in step e the temperature, T, is preferably about 5° C. to about 30° C., and more preferably about 15° C. to about 28° C. In another preferred embodiment the solids concentration is between about 0.3 to 0.35 wt % and the reaction of step e is at a temperature of about 10° to about 30° C., and for a time of 10 to 72 hours; more preferably the temperature is between 15° C. and 28° C. Typical proteolytic enzymes are selected from the group consisting of porcine mucosal pepsin, bromelain, chymopapain, chymotrypsin, collagenase, ficin, papain, peptidase, proteinase A, proteinase K, trypsin, microbial protease, and combinations of such enzymes. More preferably the proteolytic enzyme is pepsin or a microbial acid protease. When porcine mucosal pepsin is selected the pH is preferably about 1.5–3.0, and the temperature about 15° C. to about 28° C. Typically, at least 80 wt % of the insoluble collagen is converted to soluble collagen and the number average molecular weight is above 300,000 daltons; while more preferably at least 90 wt % of the insoluble collagen is converted to soluble collagen.

A further embodiment of the invention is a method for producing an aqueous solution of solubilized collagen by the steps of providing an aqueous ground slurry of insoluble collagen; adjusting the water or solid content of said wet ground slurry whereby said insoluble collagen is at a concentration that promotes substantially maximum solubilized collagen concentration that is adapted to strengthen paper in a final product; adjusting the pH of said slurry from Step b to obtain activity for a proteolytic enzyme added in Step d; adding said proteolytic enzyme to said pH adjusted slurry and reacting at a temperature, T, and for a time, t, effective for forming solubilized collagen from said insoluble collagen particles; controlling said reaction conditions for obtaining a high concentration of soluble collagen by measuring the concentration of solubilized collagen and the molecular weight of said solubilized collagen, whereby said reaction is complete when said number average molecular weight fraction above 300,000 daltons and said concentration are substantially maximized; and withdrawing said aqueous solution of solubilized collagen as product.

Feed material for the process can typically come from a variety of sources as long as the feed is relatively clean and has collagen containing material of relatively small particle size; see for example the method of Komanowsky et al discussed below. One typical method for preparing the feed material of a wet ground slurry of insoluble collagen from animal tissues includes the steps: (a) providing soft animal tissues containing collagen; (b) cleaning the collagen containing tissues to remove hair, fat, carbohydrates, and other contaminants; (c) cutting the cleaned collagen containing tissues into small pieces; (d) mixing the small pieces with water to obtain a slurry; (e) adjusting the pH of the slurry substantially near the isoelectric point of collagen from the tissues; (f) wet grinding the resulting pH adjusted slurry to obtain a slurry of insoluble collagen. The pH of this method is typically about 3 to about 7.

The invention further encompasses the unique aqueous solutions of solubilized collagen produced by the above methods.

DETAILED DESCRIPTION OF THE INVENTION

Figure 1B:
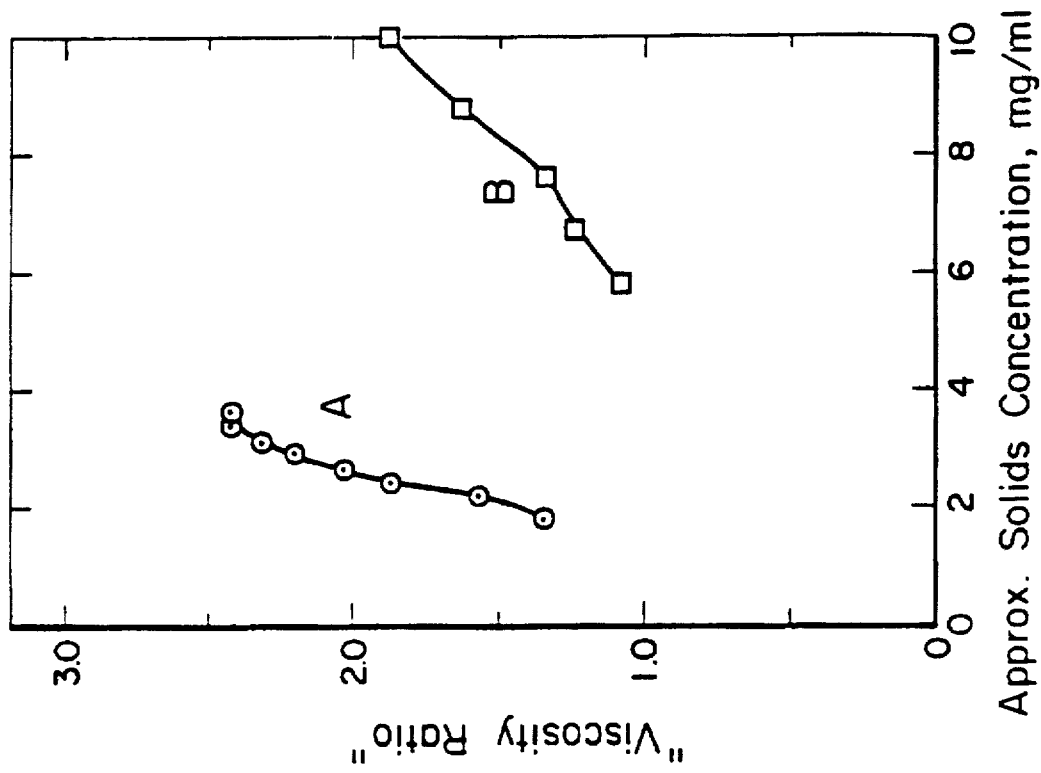
FIG. 1B is a plot showing the ratio of the viscosity determined at 20 rpm to the viscosity at 100 rpm, termed here the "viscosity ratio". The data is calculated from the data in FIG. 1A for both solubilized collagen of the invention (A) or the BA-1 collagen solutions (B).

It was recognized that solubilized collagen material, added to a cellulose pulp prior to the papermaking process (i.e. mixed with the cellulose pulp fibers in the machine chest), resulted in a significant increase in strength of the paper-collagen composite. This result is surprising since the prior art teaches that larger aggregates of collagen, such as those produced by mechanical diminution of bovine hides, is necessary. One reason that the use soluble collagen in papermaking may not have been considered is that soluble collagen can be expected to thermally denature at the fluids temperatures often employed in papermaking (greater than about 40° C.). Denatured collagen is not expected to be as useful as native collagen aggregates. It is further surprising since one would expect that the cellulose pulp could best be bound together by larger size particles such as those of the scale of the cellulose pulp itself and not those that are soluble in water. As is demonstrated in the examples herein solubilized collagen that had been centrifuged at very high gravitational forces that would remove substantially all insoluble materials was very effective in increasing the strength of paper. Further, there is no current large-scale use or commercial source for a cost effective collagen solution of this type. Small-scale applications for soluble collagen exist in the food, cosmetic and pharmaceutical industries, for which the products are much higher priced than will be economically acceptable in the cellulose pulp and paper applications of the invention.

One embodiment of the present invention achieves lower costs of operation by utilizing recycle steps to recapture and reuse enzyme that would normally be lost on removal of soluble collagen product solutions. Another embodiment of the invention also has low costs of operation but does not utilize the recycle steps to recapture enzyme. In this latter embodiment the solubilized collagen is sent directly to its end use, such as in papermaking, with no attempt to remove enzyme or otherwise purify the solubilized collagen.

DEFINITIONS

The following definitions will be useful in reading the disclosure herein:

Acidified collagen—collagen that has been treated with an acid or extracted by an acid solution.

Collagen gel—collagen that exists in its native molecular state in a continuous, highly hydrated fibrillar network.

Mechanically working—mechanical shearing of collagen-rich materials to reduce particle size and initiate gel formation.

Mixing collagen and paper pulp—mixing is at a relatively low shear rate (as compared to beating) that is conducive to the reaction of higher molecular weight collagen with cellulosic pulp so as to obtain interaction of solubilized collagen and cellulosic pulp.

Molecular weight—as used herein this term is intended to refer to number average molecular weight unless otherwise specified.

Natural collagen—collagen molecules that retain the normal triple-helical assembly of alpha-chains.

Old corrugated container—secondary cellulosic fiber obtained from cardboard boxes, corrugated cardboard, and similar Kraft paper-like sources.

Old newsprint—secondary fiber from recycled newspapers and similar sources.

Refining—a pretreatment for the paper pulp that expands and separates cellulosic pulp fibers.

Solubilized collagen—collagen that has been treated to separate the collagen fibrils to render them soluble while retaining the normal triple-helical assembly of native collagen; covalent bonds between collagen fibrils are broken so that smaller collagen molecules can go into solution; this is in comparison to mechanically worked and or acid treated collagen that merely makes the collagen pieces physically smaller but does not break the covalent bonds between fibrils; the solubilized collagen used herein has been solubilized by an enzymatic treatment that breaks the covalent bonds between collagen fibrils.

Viscosity ratio—the ratio of two viscosity measurements of a solution at two different shear rates. This is one typical way to follow the increase or decrease of viscosity due to an increase or decrease of solubilized collagen being produced from a slurry of insoluble collagen. Another typical method would be to use only the viscosity measurement to follow the increase or decrease of solubilized collagen.

The advantages of the invention are in: (1) minimizing the cost of preparing soluble collagen by processing directly from ground skin material to the maximum amount of soluble macromolecules; and (2) at the same time, maximizing the degree of conversion to soluble collagen material capable of binding to cellulosic pulp and controlling the molecular weight of the soluble collagen material in order to enhance the binding effect to the pulp fibers, thereby maximizing the resulting tensile strength and/or other mechanical properties of the paper product. Another major advantage of using the solubilized collagen over the insoluble larger aggregates of the prior art, in the production of cellulosic products such as paper, is greater uniformity in the distribution of collagen in the cellulosic pulp.

Bovine skin was selected as the collagen source in the examples described here because collagen preparation methods from skin have been widely reported, and the material is a high volume by-product of the major industries of beef production and leather manufacture; however, it is expected that collagen obtained from other sources (e.g. tendon) will work in the process also.

Collagen solubilization of skin has been accomplished by an enzymatic hydrolysis process with an animal stomach enzyme (e.g. pepsin) and several other enzymes without any other purification steps. The process results in nearly complete solubilization of ground hide preparations in 10–30 hours at room temperature in acidic solutions. Other (untested) enzymes may yield faster or cheaper conversion of collagen-containing tissues, and the process has not necessarily been optimized to minimize enzyme requirements and production time. To date, the process has been scaled to produce approximately 500 gallons of 0.3–0.4% collagen solution, and it has been demonstrated to be relatively easy to control.

EXAMPLES

The following examples, illustrative of the novel compositions and the novel methods of preparing them, are given without any intention that the invention be limited thereto.

Materials

The pepsin used was a crude (relatively unpurified) powder from pig stomach mucosa (Cat. No. P7125) purchased from Sigma Chemical Company, St. Louis, Mo. Lot #070H0437 of this product, used in the examples, contains approximately 15% protein (by UV), with an activity of 91 pepsin units/mg solids and 620 units/mg protein. Residual solids in the preparation appear to be a combination of precipitation salts, buffer salts and/or carbohydrates. Crystallized pepsin has a maximum specific activity of about 3500 units/mg protein.

Additional tests were performed with pepsin, crude powder, from Sigma Chemical Company; AFP 2000, acid fungal protease from a strain of Aspergillus niger, from Solvay Enzymes; Newlase A from a strain of Aspergillus niger, and Newlase II (from a strain of Rhizopus niveus, from Amano Enzyme U.S.A.; Quest AP, quest acid protease from a strain of Aspergillus niger, from Quest International; EDC-APA, an EDC acid protease A, and EDC-APB, an EDC acid protease B, from Enzyme Development Corporation.

The collagen slurry used herein for Examples 1–6 was prepared from ground limed-splits of bovine skin. The collagen was supplied by Teepak's Sandy Run Plant, Columbia, S.C. Typical analyses for the material of Example 6 are pH=6.4; solids content=15.67%; gelatin content= 2.62%; fat content=2.1%. A 1974 USDA report by Komanowsky, M., et al, "Production of Comminuted Collagen for Novel Applications", *J. American Leather Chem. Assoc.*, 6, 410–422 (1974), describes techniques for pre-slicing, acidifying and wet-grinding of limed splits to produce five "comminuted" (ground) collagen products, classified by extent of grinding and the resulting particle size and texture. A subsequent 1978 paper by Turkot, et al, "Comminuted Collagen: Estimated Costs of Commercial Production", *Food Tech.*, 48–57 (April, 1978), presents an economic analysis of the production costs for these same five products. The output from this plant closely approximates the ground limed-split material used as a source for collagen in the examples herein.

For Examples 7 to 11 unless otherwise provided the enzymatic collagen solubilization was performed as follows. The collagen source (either ground whole hides or ground limed splits) was ground as described in Example 7 with an 0.06 inch cutting head in a water slurry, and was spun at 4° C. in a Beckman J2-21 Centrifuge (JA-20 rotor) at 10,000 rpm for 20 minutes to remove excess liquid. This centrifuge provided a ratio of rpm to gravitation force of about 1:1, thus at 10,000 rpm the gravitational forces were about 10,000× gravity. The supernatant liquid was removed and the centrifuged solids (7.5 g) were added to a one liter Erlenmeyer flask that contained deionized water (750 mL). The suspension was stirred with a two inch magnetic stir bar and the pH was adjusted using concentrated hydrochloric acid. The enzyme was then added to the flask, which was placed in an incubator set to the desired temperature. Viscosity measurements were made by pouring approximately 100 mL of each reaction mixture into a beaker and bringing to room temperature. The viscosity was measured with a Brookfield Synchro-lectric Viscometer model RVT. Measurements were made at 20 rpm and 100 rpm with spindle No. 3. Three readings were taken at each speed and averaged for the calculation of viscosity in centipoise. Aliquots were removed for viscosity measurements at specified times and then returned to their original flasks.

A collagen solution ("BA-1"), used as a control solution in the examples below, was supplied as the soluble skin product, Secolan BA-1, by Kensey Nash Biomaterials, Exton, Pa. The solution is typically a white milky color; pH=3.1–3.3; total solids=1%±0.2%; active collagen>0.67% (nominally 1% in the examples). This product is sometimes found to be slightly gelled upon receipt. However, based on the pattern observed after electrophoretic analysis, it is believed that the BA-1 is produced by an acid-extraction process, not by an enzymatic reaction as practiced in the present invention.

It was found that the solubilization of collagen-containing solids can be effectively monitored by periodic measurement of the solution viscosity. Fluid viscosities can be conveniently measured by a variety of relatively simple methods, such as the Brookfield Model #RVT Viscometer (#3 Spindle) used with the examples. In this Brookfield system, the force exerted by a fluid upon a disk, which is rotated at constant rotational speed in the fluid, is used to estimate the fluid viscosity. In the collagen solutions described herein, the fluid viscosity will be strongly dependent on the concentration of dissolved collagen, the molecular weight distribution of the soluble collagen and the fluid temperature, and, to a lesser extent, fluid pH and ionic strength.

When the viscosity is independent of the applied force (shear), then the fluid is said to be "Newtonian". For solutions of many macromolecules, including the rod-like collagen molecules considered here, the solution viscosity is very dependent on the force applied to the liquid, and the liquid is said to be "non-Newtonian". When the dissolved macromolecules are highly elongated, and the shear rate (proportional to the rotational speed) is sufficiently high, the molecules tend to orient with the streamlines of the fluid and their effect on the fluid velocity tends to decrease in a manner that is strongly dependent on the shear rate.

Figure 1A:
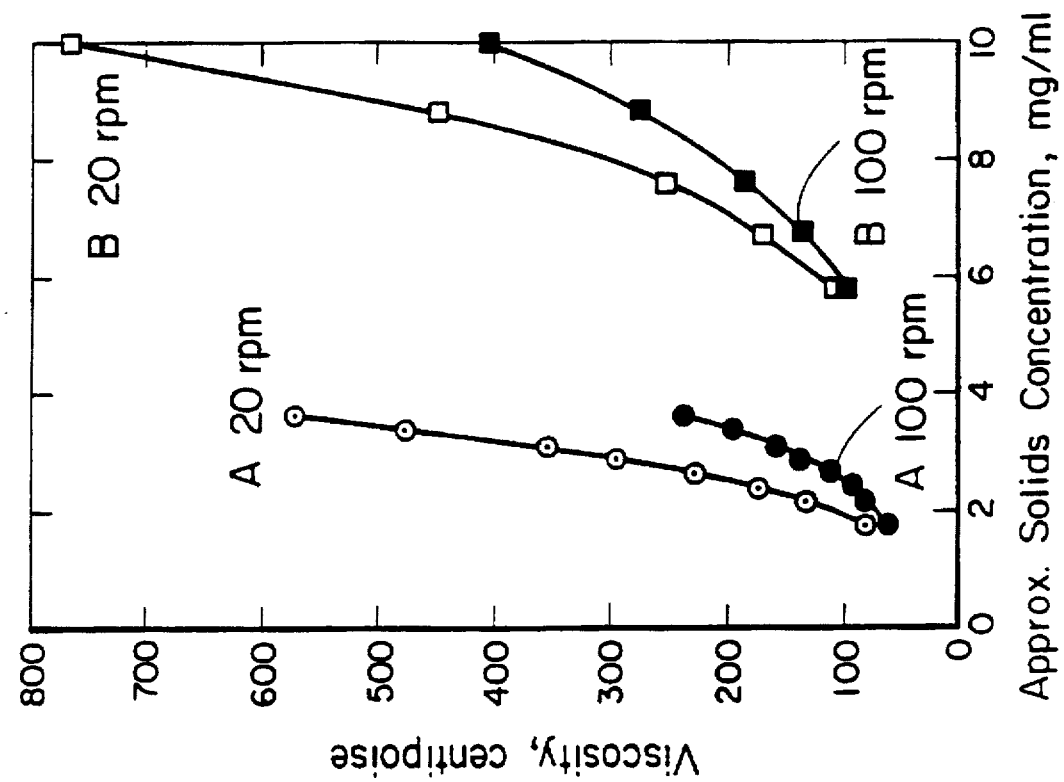
FIG. 1A is a plot showing the non-Newtonian behavior of the collagen solutions. Viscosity of diluted solutions of solubilized collagen of the invention (A) and BA-1 collagen solutions (B) at two shear rates (20 and 100 rpm).

The non-Newtonian behavior of collagen solutions is demonstrated in the experiments summarized in FIG. 1A, in which the viscosity of preparations of solubilized collagen and BA-1 were determined at room temperature as the solutions were progressively diluted with distilled water. Some uncorrected increase in solution pH may have occurred in this experiment as the samples were diluted; however, the trend for the data is valid.

For each solution, the viscosity was determined at two rotational speeds, 20 and 100 rpm. The open circles (—◯—) and filled circles (—●—) represent data for solubilized collagen of the invention at 20 rpm and at 100 rpm, respectively. The open squares (—□—) and the filled squares (—■—) represent the data for the BA-1 collagen control at 20 rpm and 100 rpm respectively. Both solutions were more viscous at the lower rotational rate, as expected. The viscosities of the collagen produced in the examples and BA-1 preparations were substantially different, with the produced collagen solution having a much higher viscosity at lower collagen concentrations and a steeper slope. These effects appear to be primarily due to the difference in the number average molecular weights of the collagen molecules in the two solutions, with the collagen solution of the invention having the larger average molecular size. The comparison shows that the method of the invention was successful in making a higher viscosity collagen material at a lower concentration thus showing the molecular weight was higher.

The ratio of the viscosity determined at 20 rpm to the viscosity at 100 rpm, termed here the "viscosity ratio", is a convenient measure of this non-Newtonian, molecular-weight-dependent effect. This is illustrated in FIG. 1B, in which the viscosity ratio is higher for collagen solutions of the invention than for BA-1. In FIG. 1B the open circles (—⊙—) represent data from the solubilized collagen of the invention and the open squares (—□—) represent data from the BA-1 collagen solution. The viscosity ratio used herein is a measure of the "degree of conversion" of solid collagen materials to soluble collagen molecules, and also a measure of molecular weight, where higher values of the viscosity ratio will correlate with the desired higher number average molecular weights of the dissolved collagen. In FIG. 1B it is important to note that since the material is being diluted, an increase in viscosity ratio is measuring the increase in concentration of soluble collagen since the molecular weight of the material remains the same. In tests of the examples below, changes in the viscosity and viscosity ratio will be measuring changes in concentration. If desired the peak soluble collagen content can be measured by chromatographic and electrophoretic techniques.

Alternatively, analysis of solubilized collagen composition was routinely performed by SDS polyacrylamide gel electrophoresis (PAGE) that used a 3% stacking gel; 6% running gel, following denaturation by boiling with β-mercaptoethanol. Some irreversible precipitation occurs during the denaturation process. Gels were stained by Coomassie Blue dye and destained in staining buffer only.

PAGE results from this technique demonstrate (results not shown here) that BA-1 solutions contain predominately tropocollagen monomer (300,000 daltons) aggregates. Collagen solutions produced by the present process that had acceptable paper binding properties appeared to have a number average molecular weight of at least 300,000 daltons, with some components having the intact triple helix of alpha, beta and gamma chains as evidenced by PAGE, other preparations may have had a disrupted helix.

Analysis of solubilized collagen composition was also routinely performed by SDS polyacrylamide gel electrophoresis (PAGE) with the Pharmacia PhastGel System. PhastGel Gradient 4–15% polyacrylamide gels were used. The buffer system in the gel is 0.112M Tris acetate, pH 6.4. PhastGel SDS Buffer Strips that contain, at pH 8.1, 0.2M Tricine, 0.2M Tris, and 0.55% SDS were used to run the gels. The separation method was from the PhastSystem Separation Technique File No. 130, Table 2.

Samples were prepared for Gel Electrophoresis by the addition concentrated stock solutions of SDS (20%) and buffers (5× stock). The final concentrations were 10 mM Tris/HCl (pH 8.0), 1 mM EDTA, 2–2.5% SDS, and 0.01% bromophenol blue. Each sample was then heated at 100° C. for 5 minutes and approximately 1 µl was applied to the gel. In some early experiments, 2-mercaptoethanol (a reducing agent) was added to the sample before heating. The addition of the 2-mercaptoethanol had no effect on the gel pattern.

At the completion of the electrophoresis, the gel(s) were stained with the Pharmacia Silver Kit. The staining method used was from the PhastSystem Silver Kit Instruction Manual, Table 2. The Development time and Background Reduction time were doubled for better visibility on the gels.

The SDS detergent in the gels disperses all non-covalent collagen aggregates leaving only covalently joined molecules. The degree to which these molecules migrate on a gel is related to their molecular weights and approximate molecular weights have been assigned to the collagen bands by co-electrophoresis of molecular weight standards on the same gels. PAGE analysis of solubilized collagen indicates bands at ~100,000 daltons (alpha-collagen), ~200,000 daltons (beta-collagen), ~300,000 daltons (gama-collagen), and bands >300,000 daltons. The intensity of the bands is in inverse order of their molecular weights.

Analysis for soluble or insoluble collagen was typically performed by first measuring the amount of hydroxyproline in the sample, then correlating this concentration with the collagen. Hydroxyproline was measured on 0.1 mL samples that were dried in polypropylene tubes at 125° C. The samples were dissolved in 0.05 mL 4M sodium hydroxide, capped, and then autoclaved for 30 minutes. Citric acid (0.05 mL of a 1.4M solution) and chloramine T reagent (1 mL of a solution that contained 1.41 g chloramine T, 10 mL 1-propanol, 10 mL deionized water, and 30 mL of a pH 6 citric acid/acetic acid buffer) were added to each tube which was then incubated for 20 min. at room temperature. PDAB solution (1 mL of a solution that contained 15 g p-dimethylaminobenzaldehyde, 62 mL isopropyl alcohol, and 26 mL 60% perchloric acid) was then added. The samples were incubated at 65° C. for 20 minutes, after which time 0.2 mL of each sample was transferred to a micro-titer plate reader and the absorbance read at 570 um. A sample of purified collagen (Vitrogen 100™; Celtrix) that contained 3.0 mg/mL collagen was found to contain 0.33 mg/mL hydroxyproline. Using this collagen preparation as a standard, multiplication of the hydroxyproline concentration by a factor of 9.1 will yield the collagen concentration.

High pressure liquid chromatography (HPLC) was performed to analyze the intact soluble collagen molecular weight distribution. HPLC was performed with a TOSOHAAS TSK-GEK G6000PW column (30 cm×7.8 mm) on a Waters 650 Advanced Protein Purification System. Absorbance was monitored at 220 mm with a flow rate of 0.25 mL/Min. (unless noted otherwise). The mobile phase contained 10 mM hydrochloric acid. A column prefilter was used with a 10 um frit.

Eluent fractions containing the HPLC peaks were analyzed by PAGE electrophoresis to determine the size of the constituent collagen molecules. The SDS in the gels disrupts the collagen aggregates so that only the molecular weights of covalently attached molecules can be determined by this method. The first eluting peak (Peak 1) contains molecules with number average molecular weights greater than 300,000 daltons as well as molecules with number average molecular weights of ~200,000 daltons and ~100,000 daltons. The smaller molecules appear to be constituents of larger aggregates that were disrupted by the SDS. The second eluting peak (Peak 2) contained molecules with number average molecular weights of ~300,000 daltons, ~200,000 daltons and ~100,000 daltons. The 200,000 dalton and 100,000 dalton molecules appear to be part of 300,000 aggregates that were disrupted by the SDS detergent. The third eluting HPLC peak (Peak 3) contains collagen fragments with number average molecular weights less than ~100,000.

In the examples below, it was determined that ground limed splits of beef hide can be nearly completely solubilized when they are subjected to pepsin hydrolysis at pH in the range of 2.0–2.2. Batch reaction times are typically 10–30 hours at room temperature (22°–26° C.). The maximum concentration of soluble collagen typically produced in this process is approximately 0.30–0.40% (3–4 mg dissolved collagen/ml). The process has been demonstrated at up to 2.0 liter-scale and, using essentially the same recipe, at approximately 500-gal scale, as discussed below. Microbial proteases gave similar results as discussed below.

EXAMPLE 1

Approximately 15 g of wet Teepak collagen solids were suspended by magnetic stirrer in 750 ml of Columbus, Ohio tap water at room temperature. The solution pH was adjusted to 2.1 with concentrated hydrochloric acid (HCl)—approximately 65–70 drops. Crude pepsin powder (0.38 g) was then added with stirring into the collagen suspension to initiate the reaction. The suspension was stirred overnight, during which heating of the solution to 26°–27° C. or higher sometimes occurred due to conduction from the stirrer plate. The viscosity of the solution was measured (20 & 100 rpm) periodically during the second day of the reaction until a maximum in the viscosity ratio was achieved, at which time the solution was stabilized by increasing the pH to 3.0–3.5 and/or by placing the solution in the refrigerator. Increasing the pH above 4.0 may initiate irreversible gelation of the collagen solution.

Figure 2:
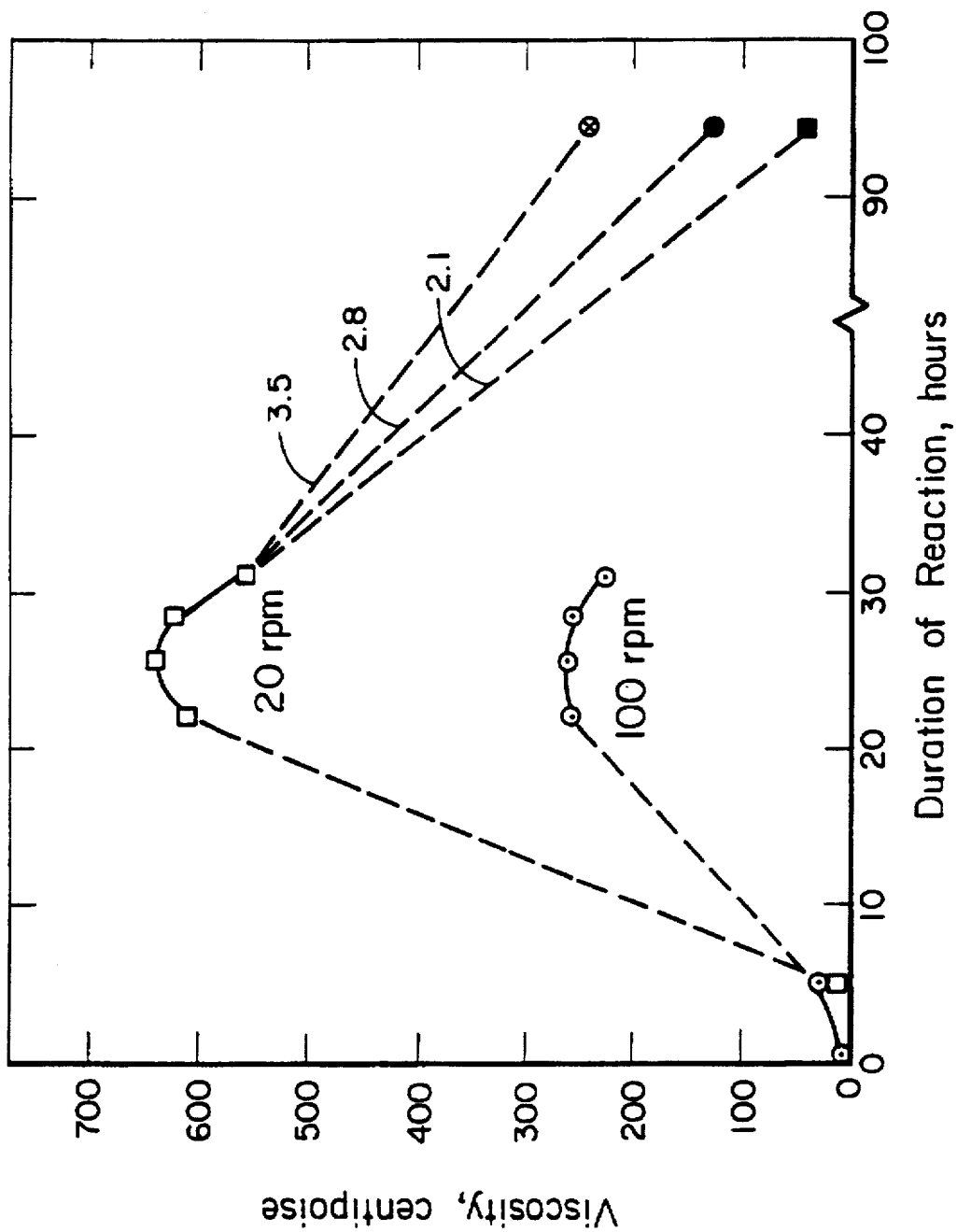
FIG. 2 is a plot of the data for Example 1 showing the viscosity at 20 rpm and 100 rpm.

Results for Example 1 are plotted in FIG. 2. FIG. 2 shows a plot of viscosity, (in centipoise) as a function of time reaction (in hours). Viscosity measurements were taken at 20 rpm (squares) and 100 rpm (circles). After completion of the reaction at pH 2.1, three samples were taken and the pH adjusted to 2.1 (—■—), 2.8 (—●—), and 3.5 (—(x)—). Viscosity tests at 20 rpm taken several days later confirmed that the samples at pH=3.5 were indeed more stable and retained more of the original viscosity than those at pH=2.1.

EXAMPLE 2

Hydrolysis of Teepak collagen at temperatures between 30°–35° C. was investigated in a series of approximately 10 experiments to determine the potential for minimizing pepsin usage in the solubilization process. Typically, enzyme-catalyzed reaction rates will double with every 5°–10° C. increase in temperature. In these experiments, a 4-liter stainless steel beaker was wrapped with heating tape, then insulated with asbestos tape. The solution temperature was controlled by a Variac in line with the heating tape to about ±1°–2° C. The process above was scaled to 2 liters of reaction volume, and a range of lower pepsin concentrations and heating profiles was investigated. In nearly all cases, complete solubilization of the Teepak solids was accomplished in 10–15 hours, and in no case was substantial viscosity developed in the solubilized product.

Typical of the ten experiments is the following: 2 liters of water were added to a beaker, to which was added 40 g of Teepak collagen, then the pH was adjusted to 2.13 with concentrated HCl, and finally 1.0 g crude pepsin was added. Initially the bath temperature was 30.0° C., about 2.5 hours later the temperature was 33° C. and the viscosity at 100 rpm was 19 cps, and about 5.5 hours later the temperature was 36.5° C. with a viscosity of 8 cps. The sample was completely solubilized in less than 8 hours at 33°–36° C. with no increase in viscosity indicating the production of a higher molecular weight material. These experiments demonstrate that it is expected to be more difficult to conserve pepsin in this process by operating at higher reaction temperatures, even early during the hydrolysis process. The maximum feasible temperature for accumulating this particular large molecular weight collagen appears to be about 30° C.

EXAMPLE 3

Figure 3:
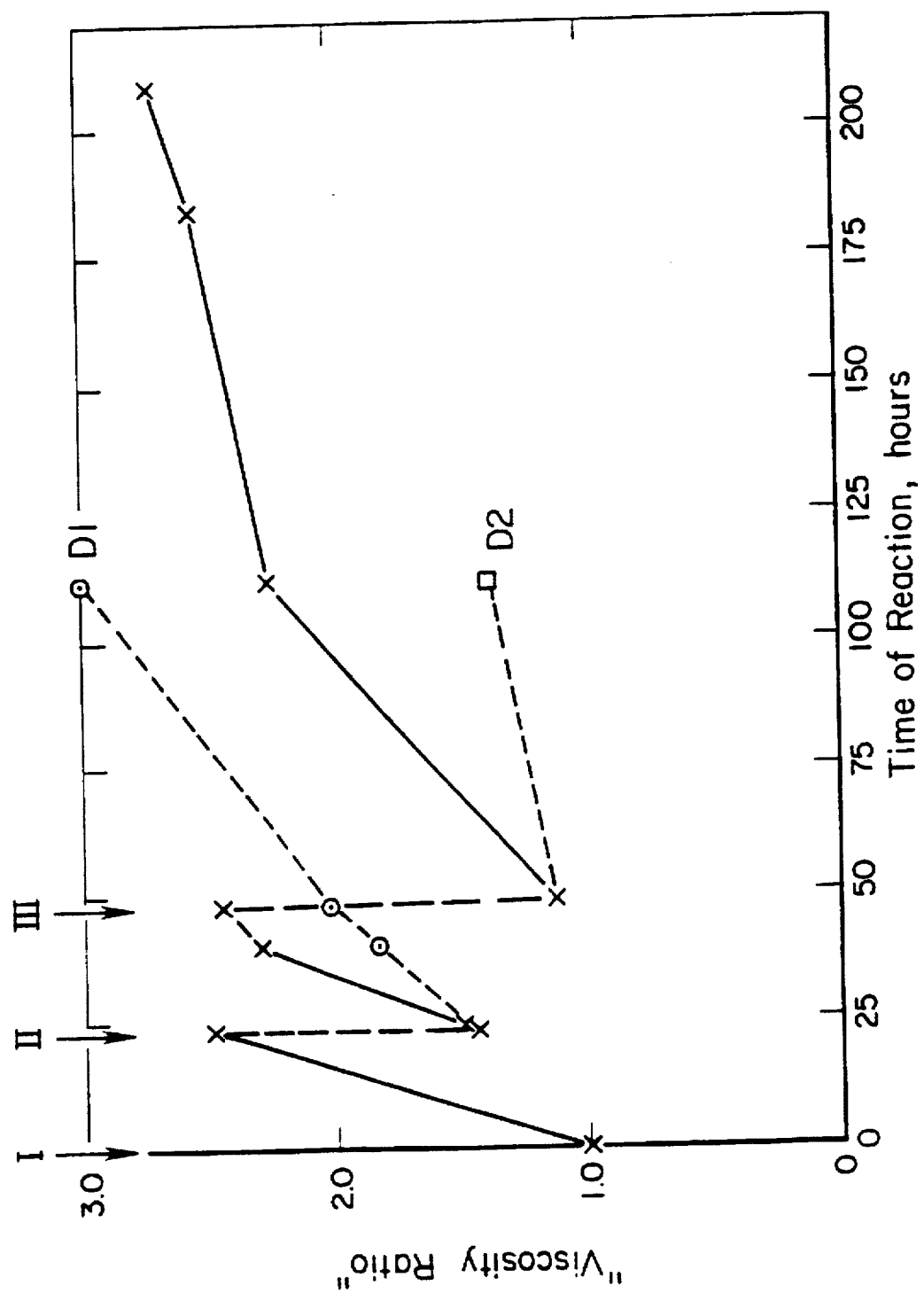
FIG. 3 is a plot of a small-scale batch collagen solubilizing reaction demonstrating the pepsin recycle of Example 3.

Another approach for minimizing pepsin usage in the process is illustrated by the experiment summarized in FIG. 3. In this experiment, the recipe above (750 ml Columbus, Ohio tap water, 15.5 g teepak collagen, 0.38 g pepsin, pH=2.1) was mixed on Day 0 to initiate the reaction in a 2-liter flask at room temperature (Roman numeral I). After approximately 1 day, an additional 750 ml of water and another charge of Teepak collagen solids (16.1 g) were added, but no additional pepsin was added to the reactor (Roman numeral II). The flask was stirred for about 5 minutes to mix the contents and the pH was readjusted with 30 drops of concentrated HCl, then the stirrer was turned off and the solids were permitted to settle out. After approximately 30 minutes, 750 ml of supernatant, "Day 1" supernatant (D1), was decanted into another flask, and stirring of both flasks was resumed. The Day 1 Supernatant contained some fine collagen particles, but it contained a much lower suspended solids load than the bottom fraction. The same process of dilution (755 ml water), collagen solids addition (15.2 g Teepak collagen), pH adjustment with 30 drops concentrated HCl (Roman numeral III), and supernatant decanting of "Day 2" supernatant (D2) was repeated in the first flask after approximately 2 days of reaction.

The progression of the hydrolysis reaction is illustrated by the solid lines (—x—) in FIG. 3. The circles (—○—) show a plot of the progression hydrolysis reaction of the Day 1 supernatant while the squares (—□—) show a plot of the Day 2 supernatant. In this example three typical charges of Teepak collagen were hydrolyzed by a single charge of pepsin, although the rate of hydrolysis appears to be decreasing with each cycle. Because the viscosity ratios of both the Day 1 and Day 2 supernatants appeared to increase after they were decanted from the main reactor, it was apparent that some pepsin and insoluble collagen was transported along with the supernatant. However, it appears that the pepsin has a higher affinity for solid collagen particles than for soluble collagen, thus most of the enzyme can be recycled several times before it is removed from the system, thereby minimizing the cost of this reagent. Preferably better separation of liquid and solids is obtained if the supernatant is separated from the insoluble collagen by centrifugation.

Most preferably a steady state in the processing recycle steps is desired. This is achieved by adding additional enzyme after the product removal step, when the rate of reaction in the recycle steps decreases below a predetermined level. Most preferably, additional enzyme is added that just replaces that lost with the removal of product.

EXAMPLE 4

An experiment was conducted in which 750 ml whitewater (recycle water from a papermaking process) was substituted for the tap water in the standard recipe of Example 3 above. Then 15.5 g Teepak collagen were added, the pH was adjusted to 2.14 with 40 drops of concentrated HCl, and 0.375 g of pepsin were added. Because the room temperature was elevated during this experiment, the reaction was conducted at 29°–31° C., and the solubilization appeared to proceed more quickly than standard reactions at 25°–26° C. In this single reaction, good viscosity was developed, the solids were nearly completely solubilized, and there appeared to be no problem with conducting the process in this solution (see Table 1). Recycling whitewater from a papermaking process in this way will greatly diminish the amount of water introduced to the process.

TABLE 1

Solubilized Collagen Made in Whitewater From Paper Making

| Time (Hours) | Viscosity 20 rpm | Viscosity 100 rpm | Viscosity Ratio |
|---|---|---|---|
| 0 | — | — | — |
| 18.5 | 415 | 177 | 2.34 |
| 22 | 440 | 186 | 2.37 |
| 26.7 | 365 | 166 | 2.20 |
| 42 | 280 | 136 | 2.06 |

EXAMPLE 5

In this example, 500 gal of Savannah, Ga. tap water was delivered to a double-paddle, 600 gal. stainless steel tank, and 75# of Teepak collagen (13.5# solids @ 18% solids) was dispersed in the water. Approximately 1.4 liters of concentrated HCl was added to bring the pH to 2.14. Pepsin (1.01 kg; Sigma Lot #70H0437) was slowly added, then the tank was covered with polyethylene film and the tank was stirred overnight. After approximately 20 hours, hydrolysis was incomplete (viscosity ratio=1.32). Because the liquid and room temperatures were relatively low (approximately 20° C.), it was decided to attempt to raise the liquid temperature by putting live steam onto the outside bottom of the tank. The steam was used for about 2.5 hours, by which time the liquid temperature was 23° C., the viscosity ratio was 2.15, and the steam heating was discontinued.

At approximately 31 hours, the viscosity ratio was 2.43, which is relatively high for this reaction. It was decided to adjust the pH in the tank to approximately 3.0, by the addition of approximately 450 grams of NaOH flakes, in order to stabilize the solution (slow/stop the pepsin reaction) for use in paper the next day. Approximately 55 gal of the pH=2.1 solution were saved in 5-gal containers prior to the pH adjustment. Because the viscosity ratio dropped slightly overnight for the pH=2.1 solution (open circles, —⊙—, in FIG. 4 and denoted by A) compared to the pH=3.0 solution (closed circles, —●—), it is concluded that pH adjustment is helpful in maintaining the highest possible molecular weight in the product during storage at room temperature.

After approximately 24 hours of reaction, some floating solid material (presumed to be fat because of its low density) was observed on the upper surface of the collagen solution near the mixer shaft. Although no attempt was made in this experiment to remove this residue, it can be easily skimmed from the preparation if the residual fat was found to be detrimental to collagen performance.

Prior to using the collagen solution made in this example and in Example 6, described below, the solution was filtered by passing it through a knitted plastic screen with openings approximately 1×3 mm, in order to remove a small number of very slowly degrading skin particles. These particles are characteristically the last material to be dissolved by pepsin and can often be found in the 3–5 mm size range. A large sample of these residual particles was filtered from the collagen solution and their dry weight was measured. Based on projecting this sample to the entire batch of collagen solution, it was estimated that more than 95% of the initial solids were solubilized in this process.

EXAMPLE 6

Figure 4:
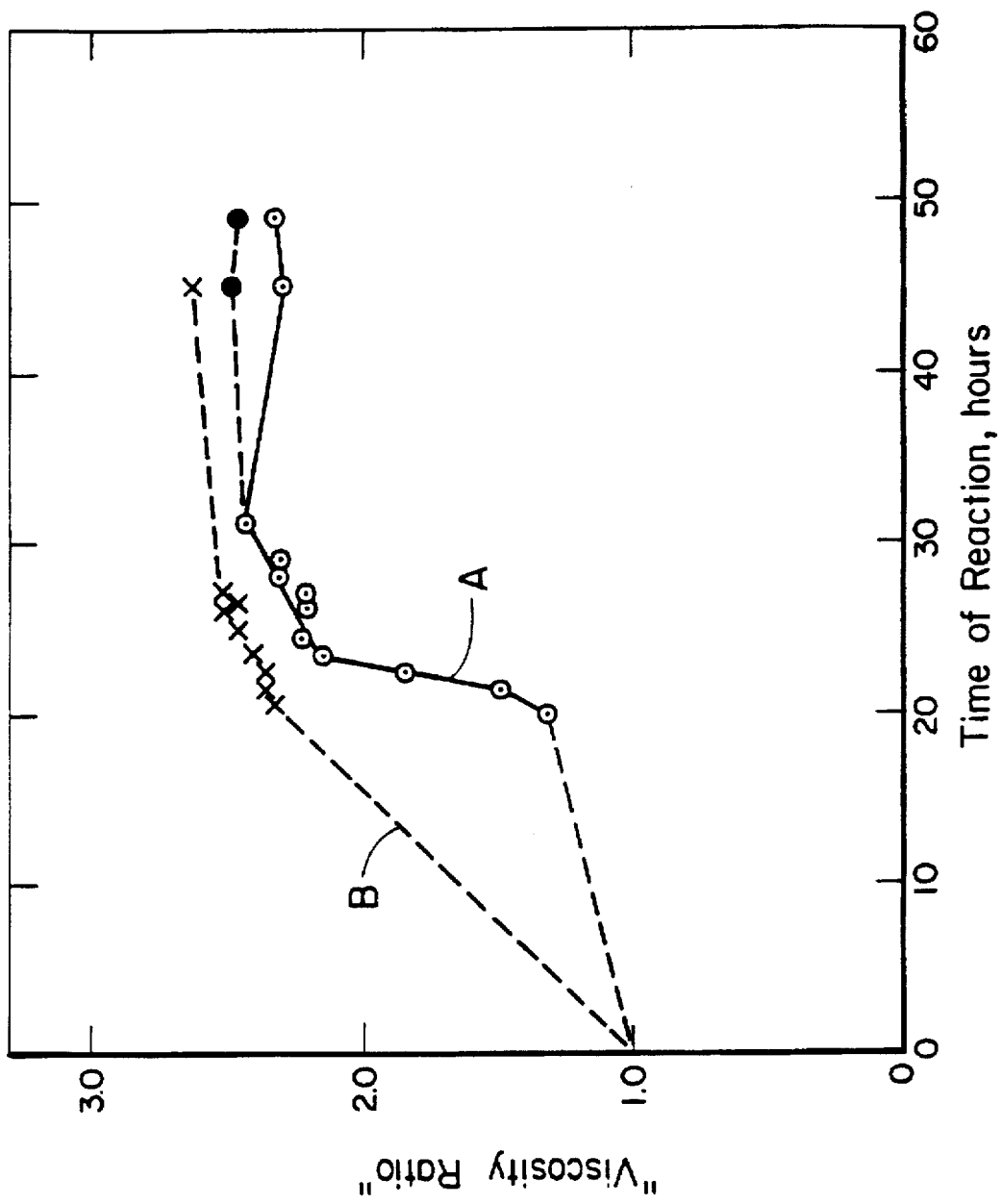
FIG. 4 is a plot of the development of viscosity ratios in Examples 5 (denoted by A) and 6 (denoted by B).

In this example, the same tank was filled with 500 gal of Savannah, Ga. tap water, which in January was very cold—about 11° C. Teepak collagen (79.5#; 12.5# of solids at 15.67% dry wt.) was dispersed in this water, then 1.5 liters of concentrated HCl was added to bring the pH to 2.18. Pepsin (1.01 kg; Sigma Lot #70H0437) was slowly added, then the tank was covered with polyethylene film. Live steam was placed on the outer bottom of the tank for approximately 4 hours to raise the liquid temperature from 11.5° to 25° C. At this time the pH was 2.40; an additional 0.4 liters of concentrated HCl was added to bring the pH down to 2.29. The tank was draped with polyethylene film to insulate the tank overnight. After approximately 28 hours the viscosity ratio was 2.51, with the temperature at about 22° C. at pH=2.46. Approximately 600 g of flaked NaOH was added to bring the tank contents to pH=2.98, the tank was covered as before and stirred overnight. The final viscosity ratio was 2.61. Results are shown in FIG. 4 at B (—x—).

Since the collagen solution in Example 6 was produced at about a 2°–3° C. higher reaction temperature during the first day than that in Example 5, the reaction appears to have progressed more rapidly, reaching completion about 4–5 hours sooner. When the pH was adjusted to about 3.0 the final solution appears to have slowed the enzymatic reaction so that little degradation of the soluble product was observed overnight.

The process is intended to produce nearly complete conversion of beef hides to a collagen solution using an enzymatic hydrolysis reaction. Objectives for the process are production of soluble collagen product at the maximum yield, while conversion costs and fixed capital expenditures are minimized. The process is not intended to produce food or medical-grade soluble collagen, and therefore requirements for production of clean solutions are minimal, and no purification of the soluble collagen is anticipated. No attempt has been made to remove the remnants of the other skin components (fat, proteoglycans, other proteins, salts, etc.), which are present in the ground-split feedstock at concentrations lower than collagen.

The process will require a series of cutters and grinders to reduce the feedstock limed splits to a shredded material that can be readily converted to soluble collagen. As cited above, the "front end" of the process will likely look similar to the USDA process for producing comminuted collagen. Depending on the pretreatment of the hides employed to prevent microbial growth, the hides may need to be delimed or acidified to remove residual calcium salts or other biocides. The ground solids are then mixed with process water (perhaps a reduced-solids whitewater stream from a paper plant), the pH is titrated to 2.0–2.2, and enzyme is added to begin the solubilization process. Following conversion, the soluble solids can be pumped directly to a paper making process and mixed with refined pulp solids or stabilized and stored.

In small-scale tests, maximum interaction between collagen and pulp solids appears to result if the pH of the solution is about 4.0 or less and the pulp consistency is 1.0% or lower. Therefore, adjustment of the pulp in the holding tank to about pH 4.0 or less appears to be beneficial although a typical run was at pH 5–6 because the paper was more stable.

EXAMPLE 7

"USDA" feed collagen materials were prepared using the method of Komanowsky et al., cited herein, as follows. Two limed splits and one dehaired and limed hide were rolled up and cut to yield 12 inch wide strips. These strips were passed through a strip cutter and then through a rotary knife cutter. An acidic solution was prepared by dissolving 102.15 g of benzoic acid in 1021.5 g of propionic acid. Acidification was carried out in 55 gallon stainless steel tumbling drums by adding 203 lbs of water and 521 g of the above acid solution to the material from the limed hide splits and 235 lb of water and 603 g of acid solution to the whole hide material. The drums were tumbled 15 minutes per hour for four hours. The final pH values were 5.1 and 5.2, respectively. Finally, part of both materials was passed through a 0.06 inch cutting head of the Urschel Comitrol. The remaining part was passed through an 0.200 inch cutting head. The products were poured into small plastic bags and placed into a freezer at −20° C. for later use.

EXAMPLE 8

USDA ground limed splits were centrifuged at 4° C. for 20 minutes at 10,000 rpm. The supernatant liquid was removed and the centrifuged limed splits (15 g) were added to a 2 L Erlenmeyer flask that contained deionized water (1500 mL). The suspension was stirred with a magnetic stirrer (2 inch stir bar) and the pH was adjusted to pH 2.1 with concentrated hydrochloric acid. Pepsin (0.76 g) was added to the flask, which was then stirred in an incubator set to 18° C. Aliquots of the reactions (100 mL) were removed at different times and analyzed for viscosity (Table 2). The pH of each aliquot was adjusted to between pH 3 and pH 3.5 and the samples were stored at 4° C. After the last aliquot was taken (50 hours), analytical samples (0.7 mL) were combined with pH 3.5 acetic acid (1.4 mL) and ultracentrifuged for 1 hour at 45,000 rpm at 4° C. The supernatants and pellets (after being re-suspended in the original volume of buffer) were analyzed for hydroxyproline as shown in Table 2.

Larger samples of the different fractions (50 mL) were combined with pH 3.5 acetic acid (100 mL) and centrifuged at 20,000 rpm for 4 hours at 4° C. The samples were stored at 4° C. for 9–10 days when they were used to make paper.

TABLE 2

Summary of Results for Example 8

| Sample Time (hrs) | Viscosity (20 rpm) (cps) | Hydroxy-Proline in Supernatant (mg/mL) | Hydroxy-Proline in Pellet (mg/mL) | ΔTS (% change from Control with no Addition) |
|---|---|---|---|---|
| 3 | 35 | 0.10 | 0.28 | 15 |
| 7 | 400 | 0.15 | 0.18 | 17 |
| 11 | 1055 | 0.23 | 0.12 | 21 |
| 15 | 1030 | 0.28 | 0.06 | 31 |

TABLE 2-continued

Summary of Results for Example 8

| Sample Time (hrs) | Viscosity (20 rpm) (cps) | Hydroxy-Proline in Supernatant (mg/mL) | Hydroxy-Proline in Pellet (mg/mL) | ΔTS (% change from Control with no Addition) |
|---|---|---|---|---|
| 26 | 800 | 0.29 | 0.05 | 35 |
| 30 | 745 | 0.26 | 0.05 | — |
| 50 | 605 | 0.27 | 0.04 | 27 |

This data demonstrates that collagen was increasingly solubilized in this reaction up to approximately 15 hours. This was evidenced by the increase in hydroxyproline in the supernatant, the decrease in the pellet size and hydroxyproline content on centrifugation, and by the initial increase in viscosity. The increase in soluble collagen was correlated with an increase in the tensile strength of the paper to which the collagen was added, where ΔTS represents the % increase in tensile strength above the control paper with no added collagen.

EXAMPLE 9

Teepak limed splits were centrifuged at 4° C. for 20 minutes at 10,000 rpm. The supernatant liquid was removed and the centrifuged limed splits (35 g) were added to a 4 L Erlenmeyer flask that contained deionized water (3500 mL). The suspension was stirred with a magnetic stirrer (2 inch stir bar) and the pH was adjusted to pH 2.1 with concentrated hydrochloric acid. Pepsin (1.75 g) was added to the flask, which was then stirred in an incubator set to 20.5° C. Aliquots of the reactions (200 mL) were removed at different times and analyzed for viscosity (Table 2). The pH of each aliquot was adjusted to between pH 3 and pH 3.5 and the samples were stored at 4° C. until they were used to make paper.

After 27 hours at 20.5° C., one third of the incubated collagen sample was removed and stirred at room temperature. The temperature of the incubator was then adjusted to 30° C. and the remainder of the sample was stirred at this temperature. At specified times, 200 ml samples were removed, the pH adjusted, and the samples store at 4° C. as described above. After the last aliquot was taken, analytical samples (0.7 mL) were combined with pH 3.5 acetic acid (1.4 mL) and ultracentrifuged for 1 hour at 45,000 rpm at 4° C. The supernatants and pellets (after being re-suspended in the original volume of buffer) were analyzed for hydroxyproline content. The supernatants were also analyzed by size exclusion HPLC as shown in Table 3.

TABLE 3

Summary of Results for Example 9A

| Incubation Time (hrs) | Peak Area | | | Viscosity (cps at 20 rpm) | Hydroxyproline in Supernatant (mg/mL) | ΔTS* (%) | |
|---|---|---|---|---|---|---|---|
| | Peak 1 ~31 min. | Peak 2 ~34 min. | Peak 3 ~45 min. | | | ONP | OCC |
| 5.5 | 9.0 | 14.9 | 5.7 | 25 | 0.09 | 14 | 27 |
| 21 | 17.5 | 21.0 | 9.5 | 375 | 0.17 | 27 | 42 |
| 23 | 16.4 | 24.7 | 10.1 | 425 | 0.17 | — | —f |
| 27 | 9.9 | 24.7 | 9.8 | 650 | 0.21 | 28 | 46 |
| 30* | 12.6 | 20.9 | 8.7 | 840 | 0.23 | 32 | 42 |

TABLE 3-continued

Summary of Results for Example 9A

| Incubation Time (hrs) | Peak Area | | | Viscosity (cps at 20 rpm) | Hydroxyproline in Supernatant (mg/mL) | ΔTS* (%) | |
|---|---|---|---|---|---|---|---|
| | Peak 1 ~31 min. | Peak 2 ~34 min. | Peak 3 ~45 min. | | | ONP | OCC |
| 45.5[b] | 15.9 | 23.4 | 0.7 | 1095 | 0.28 | 37 | — |
| 30[c] | 18.5 | 30.2 | 40.2 | 750 | 0.20 | 26 | 43 |
| 45.5[d] | 18.4 | 24.5 | 54.4 | 45 | 0.30 | 36 | 46 |

[a]This sample was incubated for 27 hours at 20.5° C. and for 3 hours at rt.
[b]This sample was incubated for 27 hours at 20.5° C. and for 18.5 hours at rt.
[c]This sample was incubated for 27 hours at 20.5° C. and for 3 hours at 30° C.
[d]This sample was incubated for 27 hours at 20.5° C. and for 18.5 hours at 30° C.
*ΔTS = % increase in Tensile Strength of paper over control (no collagen) made with 1% soluble collagen added to pulps made from Old News Print (ONP) or Old Corrugated Containers (OCC).
[f](—) indicates analysis not performed.

This data illustrates an increase in soluble collagen throughout the reaction as shown by increases in viscosity and hydroxyproline concentration in the supernatant fraction. The increase in soluble collagen is correlated with an increase in the tensile strength of paper to which the collagen was added. Samples kept at 30° C. after 27 hours of reaction demonstrated progressive conversion of high molecular weight collagen to degradation products (increase in HPLC peak 3), but in this case the lower molecular weight did not result in a similar decrease in tensile strength of papers to which it was added. This latter effect indicated that the collagen has a positive effect on the paper even when some of the material has been digested to relatively low molecular weights. Gel electrophoresis indicates the presence of significant concentration of approximately 200,000 dalton collagen and approximately 100,000 dalton collagen even after reaction at 30° C. for 18.5 hours. Thus, in the absence of detergent there may be significant amounts of 300,000 or higher molecular weight material. Substantial high molecular weight collagen was present as evidenced by the high areas of HPLC peaks 1 and 2 in samples indicated by footnotes c and d.

EXAMPLE 10

Two preparations of solubilized collagen were combined as follows. Each preparation was made from Teepak limed splits that were centrifuged at 4° C. for 20 minutes at 10,000 rpm. The supernatant liquid was removed and the centrifuged limed splits (35 g) were added to a four liter Erlenmeyer flask that contained deionized water (3500 mL). The suspension was stirred with a magnetic stirrer (2 inch stir bar) and the pH was adjusted to pH 2.1 with concentrated hydrochloric acid. Pepsin (1.75 g) was added to the flask, which was then stirred in an incubator set to 19° C. One preparation was incubated for 31.5 hours (final viscosity at 20 rpm=1160 cps) and the other preparation was incubated for 21 hours (final viscosity at 20 rpm=1025 cps). The two preparations were stored at 4° C., with no pH adjustment, for 6 days, then one and a half liters of each preparation were combined in a 4 liter flask, stirred to mix, and then rapidly heated to about 30° C. in a water bath. The flask was then stirred in a 32° C. incubator and, at specified times, 200 ml samples were removed, the pH adjusted to between 3.0 and 3.5, and the samples stored at 4° C. The results from this reaction and the results of tensile tests run on papers made with these materials are shown in Table 4 below.

This data demonstrates that, although not all of the collagen was initially soluble (hydroxyproline measurements increased throughout the reaction), there was a rapid decrease in collagen molecular weight throughout the course of the 30° C. reaction period as indicated, for example, by the viscosity decrease and increase in HPLC peak 3 area. This decrease in molecular weight did not effect the gain in tensile strength until all of HPLC peak 1 (number average molecular weight >300,000 daltons) and nearly all of HPLC peak 2 (number average molecular weight ~300,000 daltons) were converted to smaller fragments. Gel electrophoresis indicated the presence of a small amount of ~100,000 dalton number average molecular weight collagen even after 25.5 hours at 32° C. Most of the collagen has been converted to fragments with number average molecular weights less than 100,000 daltons by this time. HPLC analysis of this sample, which is done in the absence of detergent, indicates no peak 1 and a small of peak 2. The remaining 100,000 dalton number average molecular weight fragments seen on the gel presumably aggregate in the absence of detergent to form the 300,000 dalton triple helix seen as HPLC peak 2. It is this triple helical collagen that appears to impart the enhanced properties to the paper.

TABLE 4

Summary of Results for Example 10

| Incubation Time (hrs) | Peak Area | | | Viscosity (cps) | Hydroxyproline in Supernatant (mg/mL) | ΔTS (% Change From Control) |
|---|---|---|---|---|---|---|
| | Peak 1 ~31 min. | Peak 2 ~34 min. | Peak 3 ~45 min. | | | |
| 0 | 2.1 | 29.1 | — | 1260 | 0.28 | +48 |
| 2 | 25.8 | 25.6 | 12.5 | 705 | 0.27 | — |
| 3 | 26.8 | 24.9 | 19.3 | 520 | 0.29 | — |

TABLE 4-continued

Summary of Results for Example 10

| Incubation | Peak Area | | | | Hydroxyproline | ΔTS |
|---|---|---|---|---|---|---|
| Time (hrs) | Peak 1 ~31 min. | Peak 2 ~34 min. | Peak 3 ~45 min. | Viscosity (cps) | in Supernatant (mg/mL) | (% Change From Control) |
| 4 | 20.4 | 31.1 | 37.2 | 215 | 0.32 | +46 |
| 5 | 18.8 | 28.8 | 46.1 | 165 | 0.29 | — |
| 6 | 19.9 | 31.7 | 65.3 | 75 | 0.34 | +37 |
| 7 | 13.3 | 28.8 | 72.2 | 35 | 0.35 | +41 |
| 8 | 14.7 | 23.8 | 83.9 | 20 | 0.37 | +41 |
| 9 | 10.6 | 22.1 | 93.9 | 15 | 0.37 | +47 |
| 12.5 | 6.5 | 16.7 | 105.5 | 10 | 0.39 | +41 |
| 25.5 | 0 | 5.0 | 127.6 | 5 | 0.38 | +30 |

EXAMPLE 12

Reactions of microbial proteases with the collagen from limed splits as described above were as summarized in Tables 5 and 6:

Microbial proteases were reacted with ground limed splits from two sources at 17° C. A summary of the optimum results with regards to protease concentration and pH is shown in Table 5.

TABLE 5

Reaction of Microbial Proteases with Ground Limed Splits

| Enzyme | pH | Maximum Viscosity (20 rpm) | Hrs. to Maximum Viscosity |
|---|---|---|---|
| Newlase II (0.08 g) | 2.6 | 1840 | 18 |
| Quest AP (0.08 g) | 2.6 | 1535 | 22 |
| AFP 2000 (0.08 g) | 2.6 | 1415 | 22 |
| EDX-APA (0.08 g) | 2.5 | 1085 | 18 |

TABLE 6

Reaction of Microbial Proteases with Teepak Limed Splits

| Enzyme | pH | Maximum Viscosity (20 rpm) | Hrs. to Maximum Viscosity |
|---|---|---|---|
| Newlase II (0.075 g) | 2.6 | 1386 | 19 |
| Quest AP (0.08 g) | 2.6 | 945 | 24 |
| EDC-APA (0.08 g) | 2.5 | 745 | 20 |
| Newlase A (0.04 g) | 2.6 | 665 | 23 |
| AFP 2000 (0.08 G) | 2.6 | 515 | 41 |
| EDC-APB (0.08 g) | 3.0 | 435 | 39 |

All of the microbial proteases produce significantly viscous collagen solutions, demonstrating their use for solubilizing collagen from ground limed splits.

Collagen solutions prepared by the above examples appear to be stable at room temperature for 12-24 hours, and stability can be enhanced by increasing solution pH to 3.0-3.5 and/or by reducing the solution temperature to 5°-10° C.

The process demonstrated the feasibility of production of a low-cost soluble collagen product by the substantially complete solubilization of beef hide collagen (ground limed-splits). The process can be conducted at near-ambient conditions and is relatively easy to control. Of particular interest is the recycle method that reduces the cost of the relatively expensive proteolytic enzymes.

While the forms of the invention herein disclosed constitute presently preferred embodiments, many others are possible. It is not intended herein to mention all of the possible equivalent forms or ramifications of the invention. It is to be understood that the terms used herein are merely descriptive, rather than limiting, and that various changes may be made without departing from the spirit of the scope of the invention.

We claim:

1. A method for producing an aqueous solution of solubilized collagen comprising:
   a. providing an aqueous ground slurry of insoluble collagen and adjusting the pH of said slurry to obtain activity for a proteolytic enzyme added in Step b;
   b. adding said proteolytic enzyme to said pH adjusted slurry;
   c. reacting said slurry and enzyme of Step b and\or recycled insoluble collagen and enzyme of Step e at a temperature, T, and for a time, t, effective for forming a solution increased in solubilized collagen;
   d. adding insoluble collagen with or without additional water to said solution of Step c and mixing;
   e. separating at least some of the solution of Step d containing solubilized collagen from said insoluble collagen, whereby at least a portion of said insoluble collagen and proteolytic enzyme is recycled to Step c, and a separated solution containing solubilized collagen is withdrawn as product.

2. The method of claim 1, further comprising repeating Step c, Step d and Step e two or more times.

3. The method of claim 1, comprising a continuous process.

4. The method of claim 1, further comprising adding additional enzyme to the recycled insoluble collagen from Step e that substantially replaces enzyme removed with the withdrawal of product.

5. The method of claim 1, further comprising adding additional enzyme to the recycled insoluble collagen from Step e when the rate of reaction on recycling decreases below a predetermined level.

6. The method of claim 1, comprising stopping said reaction by
   (1) adjusting said pH to that where said proteolytic enzyme is substantially inactive; and/or
   (2) reducing the temperature to that where said proteolytic enzyme is substantially inactive.

7. The method of claim 1, further comprising in Step a, adjusting the liquid or solids content of said wet ground slurry so that said solids are adjusted to a concentration of about 0.1 to about 1.0 wt %.

8. The method of claim 1, whereby said temperature, T, comprises about 5° C. to about 30° C.

9. The method of claim 1, whereby said temperature, T, comprises about 15° C. to about 28° C.

10. The method of claim 7, whereby said solids concentration is between about 0.3 to 0.35 wt % and said reaction of Step c is at a temperature of about 10° to about 30° C., and for a time of 12 to 72 hours.

11. The method of claim 10, whereby said temperature is between 15° C. and 28° C.

12. The method of claim 1, further comprising: selecting said proteolytic enzyme from the group consisting of porcine mucosal pepsin, bromelain, chymopapain, chymotrypsin, collagenase, ficin, papain, peptidase, proteinase A, proteinase K, trypsin, microbial proteases and combinations of such enzymes.

13. The method of claim 1, further comprising: wherein said proteolytic is enzyme a microbial acid proteases.

14. The method of claim 12, further comprising: adjusting said pH to about 1.5–3.0, and said temperature to between about 18° C. to about 28° C., when porcine mucosal pepsin is selected.

15. The method of claim 1, further comprising: whereby at least 80 wt % of said insoluble collagen is converted to soluble collagen and the number average molecular weight is above 300,000 daltons.

16. The method of claim 1, further comprising: whereby at least 90 wt % of said insoluble collagen is converted to soluble collagen.

17. A method for producing an aqueous solution of solubilized collagen comprising:

a. providing an aqueous ground slurry of insoluble collagen;

b. adjusting the water or solid content of said wet ground slurry whereby said insoluble collagen is at a concentration that promotes substantially maximum solubilized collagen concentration and molecular weight in a final product;

c. adjusting the pH of said slurry from Step b to obtain activity for a proteolytic enzyme added in Step d;

d. adding and mixing said proteolytic enzyme with said pH adjusted slurry;

e. reacting the slurry of Step d and\or said recycled insoluble collagen of Step g at a temperature, T, and for a time, t, effective for forming a solution comprising solubilized collagen derived from said insoluble collagen particles;

f. adding insoluble collagen with or without additional water to said solution containing solubilized collagen in Step e and mixing;

g. separating at least some of said solution of Step f containing solubilized collagen from said insoluble collagen and returning said insoluble collagen to Step e, whereby at least a portion of said proteolytic enzyme is recycled, and a separated solution containing solubilized collagen is withdrawn as product.

18. The method of claim 17, further comprising repeating Step e through Step f two or more times.

19. The method of claim 17, comprising stopping said reaction by (1) adjusting said pH to that where said proteolytic enzyme is substantially inactive; and/or (2) reducing the temperature to that where said proteolytic enzyme is substantially inactive.

20. The method of claim 17, further comprising adding additional enzyme to said insoluble collagen from Step e that substantially replaces enzyme removed with the withdrawal of product.

21. The method of claim 1, further comprising adding additional enzyme to said insoluble collagen from Step e when the rate of reaction on recycling decreases below a predetermined level.

22. The method of claim 17, further comprising in Step b, adjusting said liquid or solids content of said wet ground slurry so that said solids are adjusted to a concentration of about 0.1 to about 1.0 wt %.

23. The method of claim 17, whereby in Step e said temperature, T, comprises about 5° C. to about 30° C.

24. The method of claim 17, whereby in Step e said temperature, T, comprises about 15° C. to about 28° C.

25. The method of claim 17, whereby, in Step b, said solids concentration is between about 0.3 to 0.35 wt % and in Step e said reaction is at a temperature of about 10° to about 30° C., and for a time of 12 to 72 hours.

26. The method of claim 25, whereby said temperature is between 15° C. and 28° C.

27. The method of claim 17, further comprising: selecting said proteolytic enzyme from the group consisting of porcine mucosal pepsin, bromelain, chymopapain, chymotrypsin, collagenase, ficin, papain, peptidase, proteinase A, proteinase K, trypsin, microbial proteases, and combinations of such enzymes.

28. The method of claim 17, further comprising: wherein said proteolytic is enzyme a microbial acid protease.

29. The method of claim 27, further comprising in Step c adjusting said pH to about 1.5–3.0 and in Step e said temperature to between about 18° C. to about 28° C., when porcine mucosal pepsin is selected.

30. The method of claim 17, further comprising: whereby at least 80 wt % of said insoluble collagen is converted to soluble collagen and the number average molecular weight is above 300,000 daltons.

31. The method of claim 17, further comprising: whereby at least 90 wt % of said insoluble collagen is converted to soluble collagen.

32. A method for producing a solution of soluble collagen, said method comprising the steps of:

a. reacting insoluble collagen with a proteolytic enzyme to produce a solution including soluble collagen;

b. separating at least some of the soluble collagen from the insoluble collagen;

c. withdrawing the soluble collagen as product; and d. returning the separated insoluble collagen to Step a, whereby at least a portion of the proteolytic enzyme is recycled.

33. A method as set forth in claim 32, whereby said insoluble collagen is provided as an aqueous ground slurry.

34. A method as set forth in claim 33, whereby the pH of said ground slurry is adjusted to provide activity for said proteolytic enzyme.

35. A method as set forth in claim 32, further comprising repeating Steps b, c and d two or more times.

36. A method as set forth in claim 32, further comprising adding additional insoluble collagen, with or without water or additional proteolytic enzyme, to the reacted solution of Step a, whereby said proteolytic enzyme reacts with said additional insoluble collagen.

37. A method as set forth in claim 32, further comprising adding additional water and proteolytic enzyme to Step a to the recycled insoluble collagen from Step d, so that enzyme removed with the withdrawal of said soluble collagen product is replaced.

38. A method as set forth in claim 32, further comprising adding additional proteolytic enzyme to the recycled insoluble collagen from Step d, when the rate of reaction on recycling decreases below a predetermined level.

39. A method as set forth in claim 32, wherein the insoluble collagen and proteolytic enzyme are reacted at a temperature, T, and for a time, t, effective for forming a solution increased in soluble collagen.

40. A method as set forth in claim 32, further comprising stopping said reaction by
    (a) adjusting the pH of said solution to that where said proteolytic enzyme is substantially inactive; and/or
    (b) reducing the temperature of said reaction to that where said proteolytic enzyme is substantially inactive.

41. A method as set forth in claim 33, further comprising adjusting the liquid or solids content of said aqueous ground slurry so that the solids concentration is between about 0.1 to about 1.0 wt %.

42. A method as set forth in claim 33, further comprising adjusting the liquids or solids content of said aqueous ground slurry so that the solids concentration is between about 0.3 to about 0.35 wt %.

43. A method as set forth in claim 41, wherein said temperature, T, is between about 5° C. and about 30° C.

44. A method as set forth in claim 41, wherein said temperature, T, is between about 15° C. and about 28° C.

45. A method as set forth in claim 44, wherein said temperature, T, is between about 10° and about 30° C., and said time, t, is about 12 to about 72 hours.

46. A method as set forth in claim 45, wherein said temperature, T, is between about 15° C. and about 28° C.

47. A method as set forth in claim 32, further comprising: selecting said proteolytic enzyme from the group consisting of porcine mucosal pepsin, bromelain, chymopapain, chymotrypsin, collagenase, ficin, papain, peptidase, proteinase A, proteinase K, trypsin, microbial proteases and combinations of such enzymes.

48. A method as set forth in claim 47, wherein said proteolytic enzyme is a microbial acid protease.

49. A method as set forth in claim 47, further comprising: adjusting pH to about 1.5 to about 3.0, and temperature to between about 18° C. and about 28° C., when porcine mucosal pepsin is selected.

50. A method as set forth in claim 32, whereby at least about 80 wt % of said insoluble collagen is converted to soluble collagen and the number average molecular weight of said soluble collagen is above about 300,000 daltons.

51. The method as set forth in claim 32, whereby at least about 90 wt % of said insoluble collagen is converted to soluble collagen.

52. The method as set forth in claim 33, further comprising adjusting the liquid or solids content of said aqueous ground slurry, whereby said insoluble collagen is at a concentration that promotes substantially maximum concentration and maximum molecular weight in said soluble collagen product.

* * * * *